United States Patent
Prokopuk et al.

(10) Patent No.: US 10,603,224 B2
(45) Date of Patent: Mar. 31, 2020

(54) WIRELESS SENSOR SYSTEMS AND METHODS

(71) Applicant: JPTECHNOLOGIES, INC., Aliso Viejo, CA (US)

(72) Inventors: Nicholas Prokopuk, Aliso Viejo, CA (US); Russell Edward Barber, Feasterville, PA (US)

(73) Assignee: JPTECHNOLOGIES, INC., Lake Forest, CA (US)

( * ) Notice: Subject to any disclaimer, the term of this patent is extended or adjusted under 35 U.S.C. 154(b) by 1192 days.

(21) Appl. No.: 14/772,766

(22) PCT Filed: Feb. 25, 2014

(86) PCT No.: PCT/US2014/018447
§ 371 (c)(1),
(2) Date: Sep. 3, 2015

(87) PCT Pub. No.: WO2014/137671
PCT Pub. Date: Sep. 12, 2014

(65) Prior Publication Data
US 2016/0008182 A1    Jan. 14, 2016

Related U.S. Application Data (60) Provisional application No. 61/772,993, filed on Mar. 5, 2013.

(51) Int. Cl.
*A61F 13/42* (2006.01)
*G01N 27/12* (2006.01)
*A61F 13/15* (2006.01)

(52) U.S. Cl.
CPC ...... *A61F 13/42* (2013.01); *A61F 2013/1513* (2013.01); *A61F 2013/15146* (2013.01);
(Continued)

(58) Field of Classification Search
CPC ............... A61F 13/42; A61F 2013/424; A61F 2013/426; A61F 2013/1513;
(Continued)

(56) References Cited

U.S. PATENT DOCUMENTS

| | | |
|---|---|---|
| 4,747,413 A | 5/1988 | Bloch |
| 5,760,694 A | 6/1998 | Nissim et al. |

(Continued)

FOREIGN PATENT DOCUMENTS

| | | |
|---|---|---|
| CN | 1402000 A | 3/2003 |
| CN | 102724938 A | 10/2012 |

(Continued)

OTHER PUBLICATIONS

Chang et al., Implementing RFIC and sensor technology to measure temperature and humidity inside concrete structures, Construction and Building Materials, Jun. 18, 2011, 10 pages.

(Continued)

*Primary Examiner* — Brian Wilson
(74) *Attorney, Agent, or Firm* — Knobbe, Martens, Olson & Bear, LLP (57) ABSTRACT

Incontinence management systems, methods, and sensors are provided that alert the caregiver when a patient's brief has been soiled. A resonant circuit includes a polyaniline/carbon black (PANI/CB) composite chemiresistor which undergoes a large impedance change upon exposure to the vapor or 'smell' of urine or feces. Due to the impedance change of the PANI/CB resistor, characteristics of the resonant circuit change when the sensor is exposed to urine or feces vapor. The sensor responds to an interrogating signal with a signal based least in part on the sensor's impedance and indicates the condition of the brief as soiled or clean.

26 Claims, 4 Drawing Sheets

(52) U.S. Cl.
CPC ............... *A61F 2013/15154* (2013.01); *A61F 2013/424* (2013.01); *A61F 2013/426* (2013.01); *G01N 27/126* (2013.01)

(58) Field of Classification Search
CPC .. A61F 2013/15138; A61F 2013/15154; A61F 2013/15146; G01N 27/00; G01N 27/028; G01N 27/04; G01N 27/048; G01N 27/126
USPC ...................... 340/572.1–572.7, 573.1, 573.5
See application file for complete search history.

(56) References Cited

U.S. PATENT DOCUMENTS

| | | |
|---|---|---|
| 5,790,035 A | 8/1998 | Ho |
| 5,796,345 A | 8/1998 | Leventis et al. |
| 5,808,554 A | 9/1998 | Shuminov |
| 5,838,240 A | 11/1998 | Johnson |
| 5,903,222 A | 5/1999 | Kawarizadeh et al. |
| 5,908,411 A | 6/1999 | Matsunari |
| 6,030,372 A | 2/2000 | Buell et al. |
| 6,091,336 A | 7/2000 | Zand et al. |
| 6,093,869 A | 7/2000 | Roe et al. |
| 6,097,297 A | 8/2000 | Fard |
| 6,160,198 A | 12/2000 | Roe et al. |
| 6,163,262 A | 12/2000 | Wu |
| 6,186,991 B1 | 2/2001 | Roe et al. |
| 6,200,250 B1 | 3/2001 | Janszen |
| 6,213,992 B1 | 4/2001 | Dreier |
| 6,246,330 B1 | 6/2001 | Nielsen |
| 6,384,296 B1 | 5/2002 | Roe et al. |
| 6,405,135 B1 | 6/2002 | Adriany et al. |
| 6,464,635 B1 | 10/2002 | Jimenez Cerrato et al. |
| 6,559,772 B2 | 5/2003 | Zand et al. |
| 6,580,013 B1 | 6/2003 | Belloso |
| 6,677,859 B1 * | 1/2004 | Bensen ...................... A61F 5/48 340/552 |
| 6,701,776 B2 | 3/2004 | Stetter |
| 6,756,521 B1 | 6/2004 | Breitkopf |
| 6,832,507 B1 * | 12/2004 | van de Berg ........ G01N 27/121 324/652 |
| 6,840,904 B2 | 1/2005 | Goldberg |
| 6,870,479 B2 | 3/2005 | Gabriel |
| 6,921,647 B2 | 7/2005 | Kritzman et al. |
| 7,040,139 B2 | 5/2006 | Sunshine |
| 7,145,053 B1 | 12/2006 | Emenike et al. |
| 7,221,279 B2 | 5/2007 | Nielsen |
| 7,221,280 B2 | 5/2007 | Hsieh |
| 7,285,160 B2 | 10/2007 | Zhu et al. |
| 7,295,125 B2 | 11/2007 | Gabriel |
| 7,314,752 B2 | 1/2008 | Kritzman et al. |
| 7,352,286 B2 | 4/2008 | Chan et al. |
| 7,449,614 B2 | 11/2008 | Ales, III |
| 7,551,058 B1 * | 6/2009 | Johnson ............... G01N 27/226 340/10.41 |
| 7,825,803 B2 | 11/2010 | Neff et al. |
| 7,956,759 B1 | 6/2011 | Kim |
| 7,969,307 B2 | 6/2011 | Peeters |
| 7,977,529 B2 | 7/2011 | Bergman et al. |
| 2007/0210923 A1 * | 9/2007 | Butler .................. G06K 7/0008 340/572.8 |
| 2010/0090802 A1 * | 4/2010 | Nilsson .................. G01N 17/04 340/10.1 |
| 2012/0116683 A1 * | 5/2012 | Potyrailo ............... G01N 27/02 702/19 |
| 2013/0036802 A1 * | 2/2013 | Johnson ............... G01N 27/223 73/74 |
| 2014/0011286 A1 * | 1/2014 | Potyrailo ........... G01N 33/0031 436/149 |
| 2014/0296808 A1 * | 10/2014 | Curran .................... A61F 13/42 604/361 |

FOREIGN PATENT DOCUMENTS

| | | |
|---|---|---|
| JP | 2003-139775 A | 5/2003 |
| JP | 2006-296566 A | 11/2006 |
| JP | 2011-147505 A | 8/2011 |
| WO | WO 00/20852 A1 | 4/2000 |
| WO | WO 00/79497 A1 | 12/2000 |
| WO | WO 01/18535 A2 | 3/2001 |
| WO | WO 2007/087674 A1 | 8/2007 |
| WO | WO 2011/152676 | 12/2011 |

OTHER PUBLICATIONS

Cook et al., Wireless sensor nodes, each a self-powered system performing sensing, communication, and computation, form reliable mesh networks coordinating efforts to add intelligence to the environment, Proceedings of the IEEE, Jun. 2006, 20 pages.

Garcia et al., A Review of Wireless Sensor Technologies and Applications in Agriculture and Food Industry, Sensors, Jun. 11, 2009, 23 pages.

Hurk et al., Long-term ambulatory monitoring of urine leakage in the elderly, Journal of Medical Engineering & Technology, Mar.-Apr. 1998, 3 pages.

Kazimierczuk, Class E Tuned Power Amplifier with Nonsinusoidal Output Voltage, IEEE Journal of Solid-State Circuits, Aug. 1986, 7 pages.

Ong et al., Design and application of a wireless, passive, resonant-circuit environmental mentoring sensor, Sensors and Actuators, Feb. 16, 2001, 11 pages.

Opasjumruskit et al., Self-Powered Wireless Temperature Sensors Exploit RFID Technology, IEEE CS and IEEE ComSoc, Jan.-Mar. 2006, 8 pages.

Potyrailo et al., RFID sensors as the common sensing platform for single-use biopharmaceutical manufacturing, Measurement Science and Technology, May 25, 2001, 17 pages.

Yambem et al., A New Wireless Sensor System for Smart Diapers, IEEE Sensors Journal, Mar. 2008, 2 pages.

Yang et al., Novel "Enhanced-Cognition" RFID Architectures on Organic/Paper Low-Cost Substrates Utilizing Inkjet Technologies, International Journal of Antennas and Propagation, Sep. 10, 2007, 7 pages.

International Search Report and Written Opinion for PCT/US2014/018447, dated May 27, 2014, 11 pages.

Search Report dated Mar. 7, 2018 for Chinese Application No. 20140012390.2, 2 pages.

* cited by examiner

WIRELESS SENSOR SYSTEMS AND METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Incontinence rates are reported as high as 60% for residents in nursing homes and 66% for patients in acute care. Intensive care units generally have the highest incontinence rates. Skin injuries due to incontinent-associated dermatitis (IAD) occur in a third of hospitalized patients. As many as 41% of adults in long-term care facilities experience some form of skin condition in the perineal region. IAD increases the risk of microbial skin infections and pressure ulcers, which can lead to longer hospital stays, increased treatment cost, greater risk of nosocomial infection, and higher morbidity and mortality rates. The reason for the incontinence is often unknown. In some cases, incontinence may be caused by multiple factors including treatments which cannot be discontinued in hospitalized patients.

Moreover, skin conditions are a metric of an acute care facility's quality. When applying to the American Nurses Association for Magnet Status, an acute care facility must report quarterly data on pressure ulcer prevalence. Similarly, long-term care facilities must report pressure ulcer rates and risk fines if proper actions were not taken to prevent the injuries Managing incontinence according to the Guidelines of the Wound, Ostomy, and Continence Nurses Society requires the skin be kept dry and clean and the application of skin protectant after each incontinent episode. Delays in changing a brief or diaper are cited as the leading cause of IAD, while more frequent changing of incontinence briefs was found to reduce the incidence of pressure ulcers.

However, without a method to identify when an incontinent event has occurred, caregivers are often unaware of the patient's condition. As a result perineal hygiene occurs most often by schedule rather than by need.

SUMMARY

Incontinence management systems and methods are provided that alert the caregiver when a patient's brief has been soiled. Incontinence or an incontinent event comprises an event resulting from a lack of voluntary control of an excretory function. This can occur in adults, children and infants. A bodily waste detector or sensor comprises a bodily waste sensing element or transducer and a passive resonant LC-circuit. In an embodiment, the bodily waste sensing element comprises a polyaniline/carbon black (PANI/CB) composite chemiresistor which undergoes a large impedance change upon exposure to the vapor or 'smell' of a bodily waste, such as urine or feces. Due to the impedance change of the PANI/CB resistor, characteristics of the resonant circuit change when the sensor is exposed to urine or feces vapor.

In other embodiments, other properties of the bodily waste sensing element, such as, for example, capacitance, inductance, dielectric strength, conductivity, permeability, permittivity, magnet field strength, crystalline structure, reflectivity, refractivity, photosensitivity, thermal properties, and the like, undergo a change upon exposure to urine and/or feces. Due to the change one or more of the properties, characteristics of the circuit comprising the bodily waste sensing element change when the sensor is exposed to urine and/or feces.

In other embodiments, a moisture detector comprises a moisture sensing element or transducer and a passive LC-circuit. In an embodiment, the moisture sensing element undergoes an impedance change upon exposure to moisture. Due to the impedance change, characteristics of the resonant circuit change when the sensor is exposed to moisture.

In other embodiments, other properties of the moisture sensing element, such as, for example, capacitance, inductance, dielectric strength, conductivity, permeability, permittivity, magnet field strength, crystalline structure, reflectivity, refractivity, photosensitivity, thermal properties, and the like, undergo a change upon exposure to moisture. Due to the change in one or more of the properties, characteristics of the circuit comprising the moisture sensing element change when the sensor is exposed to moisture.

With conventional RF technology, a reader or interrogator interrogates a sensor or a sensor insert placed in a patient's brief through clothing and blankets. In some embodiments, the reader reads the sensor response from a distance of up to approximately 5 meters. In other embodiments, the reader reads the sensor response from a distance that is greater than approximately 5 meters. The interrogating signal from the transponder powers the passive sensor and the sensor provides wireless communication using high frequency (HF) or ultra-high frequency (UHF) signals. In an embodiment, the sensor reflects back a signal modulated by the sensor's impedance and indicates the condition of the brief as soiled or clean. Once informed, the caregivers can provide the appropriate care in a timely fashion.

Systems and methods disclose a bodily waste sensor comprising a circuit comprising a polyaniline/carbon black (PANI/CB) chemiresistor. The circuit is energized by an interrogating radio frequency signal to produce a response signal based at least in part on an impedance of the PANI/CB chemiresistor. The impedance of the PANI/CB chemiresistor becomes greater upon exposure to bodily waste than in the absence of bodily waste. In one embodiment, the circuit is a resonant circuit. In other embodiments, the circuit is a telemetry circuit.

In accordance with various embodiments, a method of detecting an incontinent event or a bodily waste event of a person is disclosed. The method comprises providing a sensor to detect bodily waste. The sensor comprising a polyaniline/carbon black (PANI/CB) chemiresistor configured to increase impedance in the presence of the bodily waste. The methods further comprises receiving an interrogating signal at the sensor, where the interrogating signal powers the sensor, and sending a response signal from the sensor in response to the interrogating signal, where the response signal is based at least in part on the impedance of the PANI/CB chemiresistor.

In some embodiments, a bodily waste sensor is provided. The sensor comprises a resonant LC-circuit comprising a sensor and energized by an interrogating radio frequency (RF) signal to produce a response signal based at least in part on an impedance of the sensor, where the impedance of the sensor changes upon exposure to bodily waste.

For purposes of summarizing the invention, certain aspects, advantages, and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

DETAILED DESCRIPTION OF EMBODIMENTS

Several chemiresistor sensors are known to respond to chemical analytes. A polyaniline/carbon black (PANI/CB) sensor offers sensitivity to urine and feces through acid-base reactions between amines in the waste and the protonated polymer backbone of the polyaniline (PANI). The ammonia in urine, a byproduct of urea, deprotonates the PANI causing a resistance increase on the order of approximately $10^5$ ohms. In some embodiments, the resistance can increase by between approximately 10% and approximately 100,000%, and varies with the area, such as the length and the width, of the PANI/CB sensor.

Figure 1:
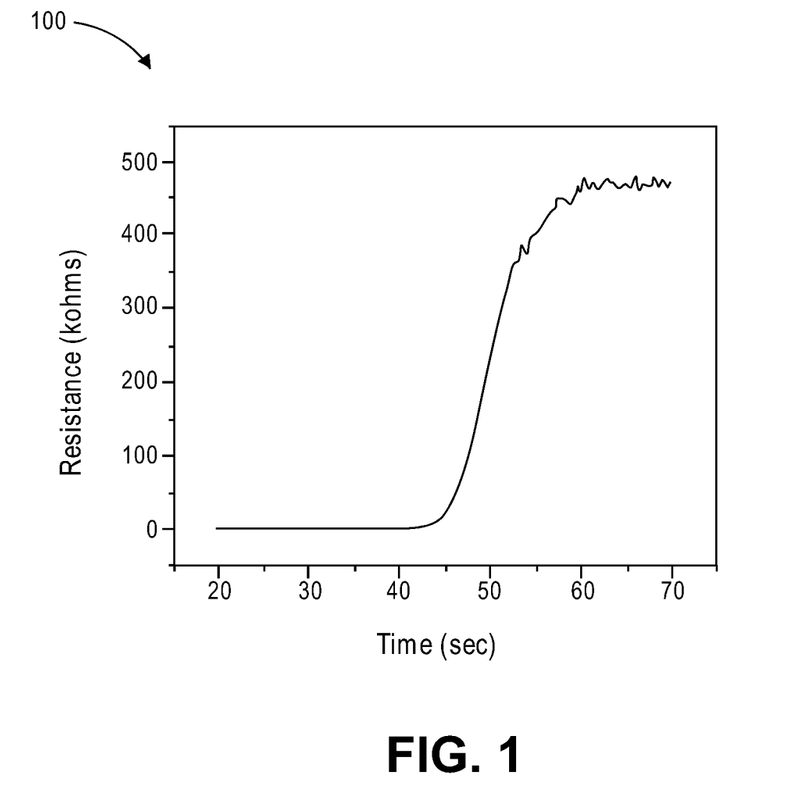
FIG. 1 is a graph illustrating exemplary resistance change of a PANI/CB sensor to urine vapor, according to certain embodiments.

FIG. 1 illustrates a graph 100 showing the resistance change of an exemplary PANI/CB sensor to urine vapor where the x-axis indicates time in seconds and the y-axis indicates resistance in kilohms. The initial resistance of the PANI/CB sensor is approximately 500 ohms. Urine vapor exposure is initiated at approximately 40 seconds. At approximately 60 seconds, the resistance of the PANI/CB sensor is approximately 470 kilohms.

PANI/CB chemiresistors are also highly selective in their response to ammonia and organic amines such as skatole (3-methylindole), which is an aromatic component of feces. Water, alcohols, and other organics only increase the polymer composite's resistance by a factor of approximately 100. This is three orders of magnitude less than the resistance changed caused by the amines.

Figure 1A:
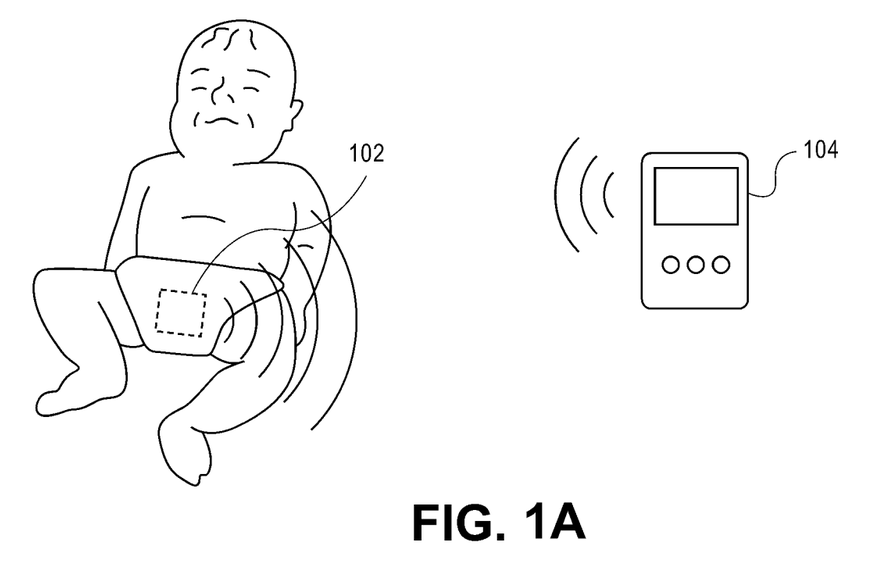
FIG. 1A illustrates an exemplary sensor and an exemplary reader, according to certain embodiments.

FIG. 1A is an illustration of a bodily waste sensor, incontinence sensor, or sensor insert 102 and a reader or interrogator 104. A transponder is a device for receiving and transmitting a signal. In an embodiment, the incontinence sensor 102 comprises a PANI/CB chemiresistor and operates as a transponder. The reader or interrogating device 104 sends an interrogating signal, such as a radio frequency (RF) signal, to the incontinence sensor 102. In one embodiment, the interrogating signal provides power to the incontinence sensor 102. The incontinence sensor reflects back to the reader 104 a signal based at least in part on the resistance of the PANI/CB chemiresistor. Based on the signal from the incontinence sensor 102, it is determined whether an incontinent event has occurred.

Embodiments of the incontinence sensor 102 reflect a signal that correlates with the impedance of the PANI/CB chemiresistor, operate passively, that is without the need for a battery or supplemental power supply, and keep the overall cost low so that the sensor insert can be treated as disposable.

Figure 2:
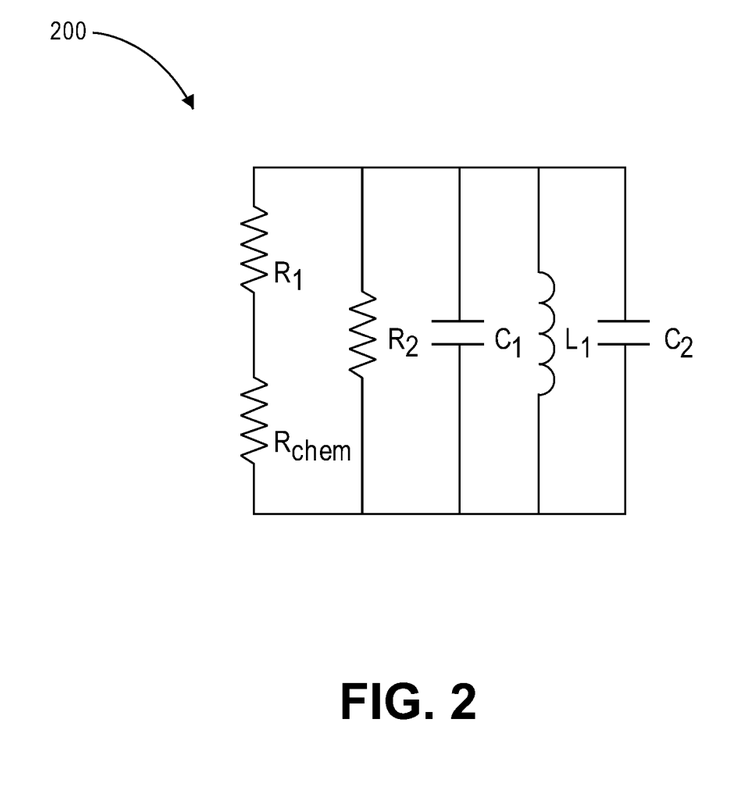
FIG. 2 is a schematic diagram of an exemplary resonant LC-circuit incorporating a PANI/CB chemiresistor, according to certain embodiments.

For a more detailed understanding of a first embodiment, reference is now made to FIG. 2. FIG. 2 is a schematic diagram of an exemplary resonant or oscillating LC-circuit 200 which transmits the sensor responses when interrogated by a radio frequency (RF) signal. Resonant circuit 200 comprises a PANI/CB chemiresistor $R_{chem}$, a first resistor $R_1$, a second resistor $R_2$, a first capacitor $C_1$, a second capacitor $C_2$, and an inductor $L_1$. Resistors $R_1$ and $R_{chem}$ electrically couple in series. The series combination of $R_1$ and $R_{chem}$ electrically couples in parallel with each of $R_2$, $C_1$, $L_1$, and $C_2$.

In the resonant circuit 200, changes in the impedance of the PANI/CB chemiresistor $R_{chem}$ are reflected in the quality (Q) factor of the circuit's response. The Q-factor, $f_0/\Delta f$, is defined as the ratio of the circuit's center frequency or resonant frequency, $f_0$, to its half-power bandwidth $\Delta f$ (i.e. the bandwidth over which the power of vibration is greater than half the power at the resonant frequency). An LC-circuit with a high Q-factor has greater amplitude (signal) at the resonant frequency but also a smaller range of frequencies or smaller bandwidth at which the oscillator resonates.

Initially, with no exposure to urine/feces vapor, the resistance of $R_{chem}$ is very low, resulting in a low Q-factor. The first resistor $R_1$ is placed in series with $R_{chem}$ to ensure that a short circuit does not occur. As the resistance of $R_{chem}$ increases due to exposure to urine/feces vapor, the oscillation of the circuit 200 is dampened less, which leads to a higher Q-factor.

The reader 104 interrogates the incontinence sensor 102 comprising the LC-circuit 200 and the sensor 102 reflects back to the reader 104 a signal based at least in part on the resistance value of the chemiresistor Rchem. In other embodiments, the circuit 200 reflects back to the reader 104 a signal when urine and/or feces are present and reflects no signal when urine and/or feces are absent. In other embodiments, the circuit 200 reflects back to the reader 104 a signal when urine and/or feces are absent and reflects no signal when urine and/or feces are present.

In some embodiments, the reader 104 determines the Q-factor of this reflected signal and determines whether an incontinent event has occurred based on the Q-factor of the signal reflected from the sensor circuit 200. In another embodiment, the reader 104 transmits the received signal to a determining device. The determining device determines the Q-factor of this reflected signal and determines whether an incontinent event has occurred based on the Q-factor of the signal reflected from the sensor circuit 200. Thus, by monitoring the Q-value of the LC-circuit 200, an incontinent event can be detected.

In some embodiments, the determining device comprises a computer processor and memory including computer-executable instructions. In a further embodiment, the reader comprises the determining device. In some embodiments, the determining device comprises an alerting system including the sensing element.

Figure 3:
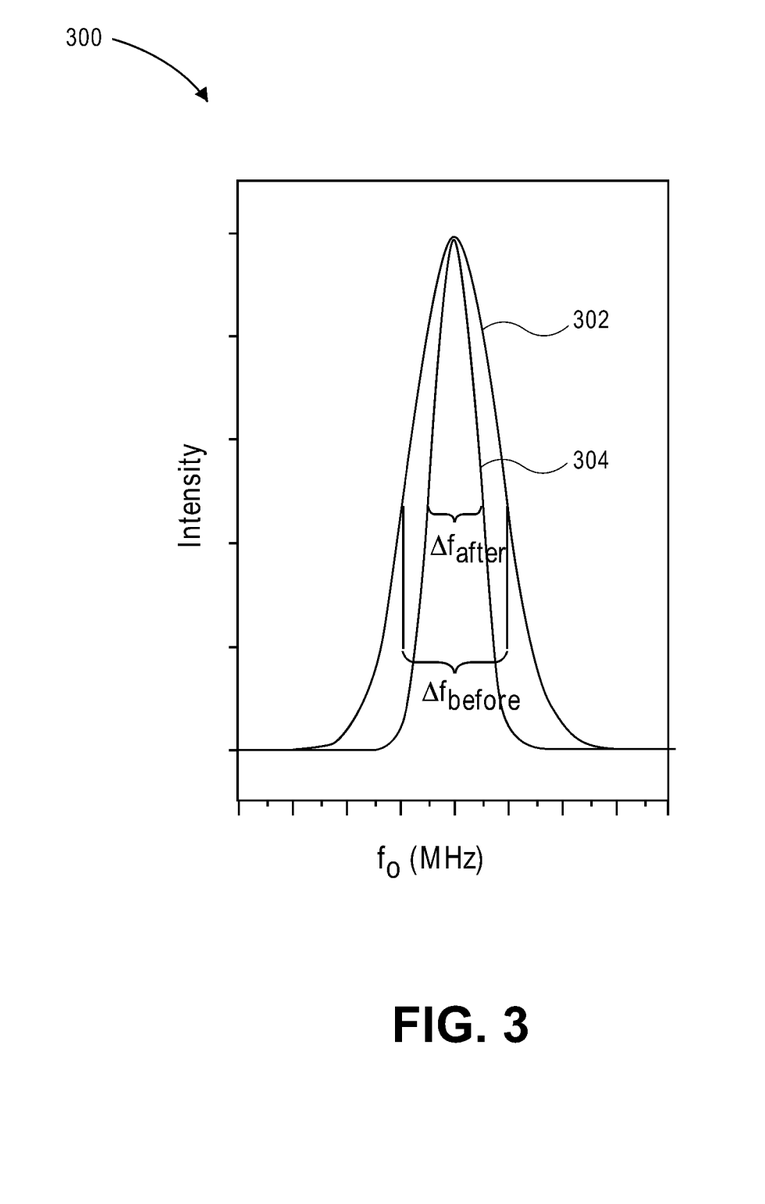
FIG. 3 is a graph illustrating a simulated sensor response upon activation of an exemplary PANI/CB sensor, according to certain embodiments.

For example, in one embodiment, $R_1$=15 kΩ; $R_2$=30.616 kΩ; $C_1$=2.8 pF; L1=5.343 uH; and C2=82 pF, and the LC-circuit 200 has a resonant frequency of approximately 6.6 MHz. FIG. 3 is a graph 300 illustrating a simulated sensor response before activation 302 and a simulated sensor response upon activation 304 of an exemplary PANI/CB sensor $R_{chem}$ in the circuit 200. In the absence of urine and feces, $R_{chem}$<<R2 and the Q-factor is approximately 60. When an incontinent event occurs, the resistance of Rchem increases such that $R_{chem}$>>$R_2$. The Q-factor of the reflected signal from the circuit 200 increases to approximately 120 indicating a positive sensor response. In one embodiment, the Q-value is proportionate to the resistance of $R_{chem}$, which then yields a precise value or an approximately precise value of the chemiresistor's impedance rather than just identifying a positive result (incontinent event) or a negative result (absence of incontinent event). Advantageously, the precise or approximately precise value of the chemiresistor's impedance can be used to determine whether the sensor is exposed to urine or feces. Further, the precise or approximately precise value of the chemiresistor's value can be used to determine false positive or false negative events.

In the above example, the Q-factor of the resonant circuit 200 upon the occurrence of an incontinent event is approximately twice the Q-factor of the resonant circuit 200 in the absence of an incontinent event, as illustrated in FIG. 3. Other embodiments of the LC-circuit 200 may comprise different values of $R_1$, $R_2$, $C_1$, $C_2$, and $L_1$, different resonant frequencies, and the change in the Q-factor of the reflected signal before activation of $R_{chem}$, and upon activation of $R_{chem}$, may be approximately a factor of 2, may be less than a factor of 2, and may be greater than a factor of 2. However, the Q-factor of the circuit 200 upon activation of the PANI/CB sensor $R_{chem}$, is greater that the Q-factor of the circuit before the activation of the PANI/CB sensor $R_{chem}$.

Advantageously, the low power requirements of the resonant circuit 200 enable the reader 104 to read the sensor insert 102 from a distance. Further, the urine/feces sensor inserts 102 comprising the LC-circuit 200 remains within the electric and magnetic fields of the reader 104 for a prolonged time, which permits the reader 104 to interrogate the sensor insert often. For example, a 6.6 MHz reader 104 can interrogate the resonant circuit 200 thousands of times per second and process the data. Operating as part of an incontinence management system, the reader 104 could make an assessment every few seconds, in one embodiment. In an embodiment, the reader 104 can take multiple readings of the sensor inserts 102 and signal average many thousand responses for an improved signal-to-noise ratio. Further yet, the electrical components of the resonant circuit 200 are low cost devices. For example, the cost of $R_1$, $R_2$, $C_1$, $C_2$, and $L_1$ in the above example are priced at approximately $0.08 per device, making for a very cost efficient system.

In further embodiments, a bodily waste sensor comprises a resonant LC circuit, such as circuit 200, for example, and a sensor element having a property that varies or changes in the presence of bodily waste. The resonant LC-circuit is configured such that it comprises a characteristic that is based at least in part on the property of the sensor element that changes in the presence of bodily waste. In response to an interrogating signal from the reader, the circuit provides a signal based at least in part on the property of the sensor element that changes in the presence of bodily waste. Thus, the bodily waste sensor provides a first signal in the absence of bodily waste and a second signal in the presence of bodily waste, where the first and the second signals are different.

Examples of the sensor element are moisture sensors, metal oxide moisture sensors, capacitance moisture sensors, electrolyte activation moisture sensors, and the like.

In another embodiment, the sensor insert 102 comprises one or more digital LC circuits. A specific ID number is assigned to each circuit. Activation of the sensor component and the resulting change in its electronic properties cause a change in the specific ID numbers transmitted by the tags or the number of numbers transmitted. For example, a tag may have two digital circuits which reflect two specific and different ID numbers when interrogated. When the sensor is activated, only one of these numbers is reflected back. In another example, an insert has a single digital LC circuit which transmits a specific ID number to the interrogator. When the sensor's electronic properties change due to a positive response to urine/feces, the ID number reflected back is different by some amount. This amount can be related to the magnitude of the change in the sensor's electronic property or not.

Figure 4:
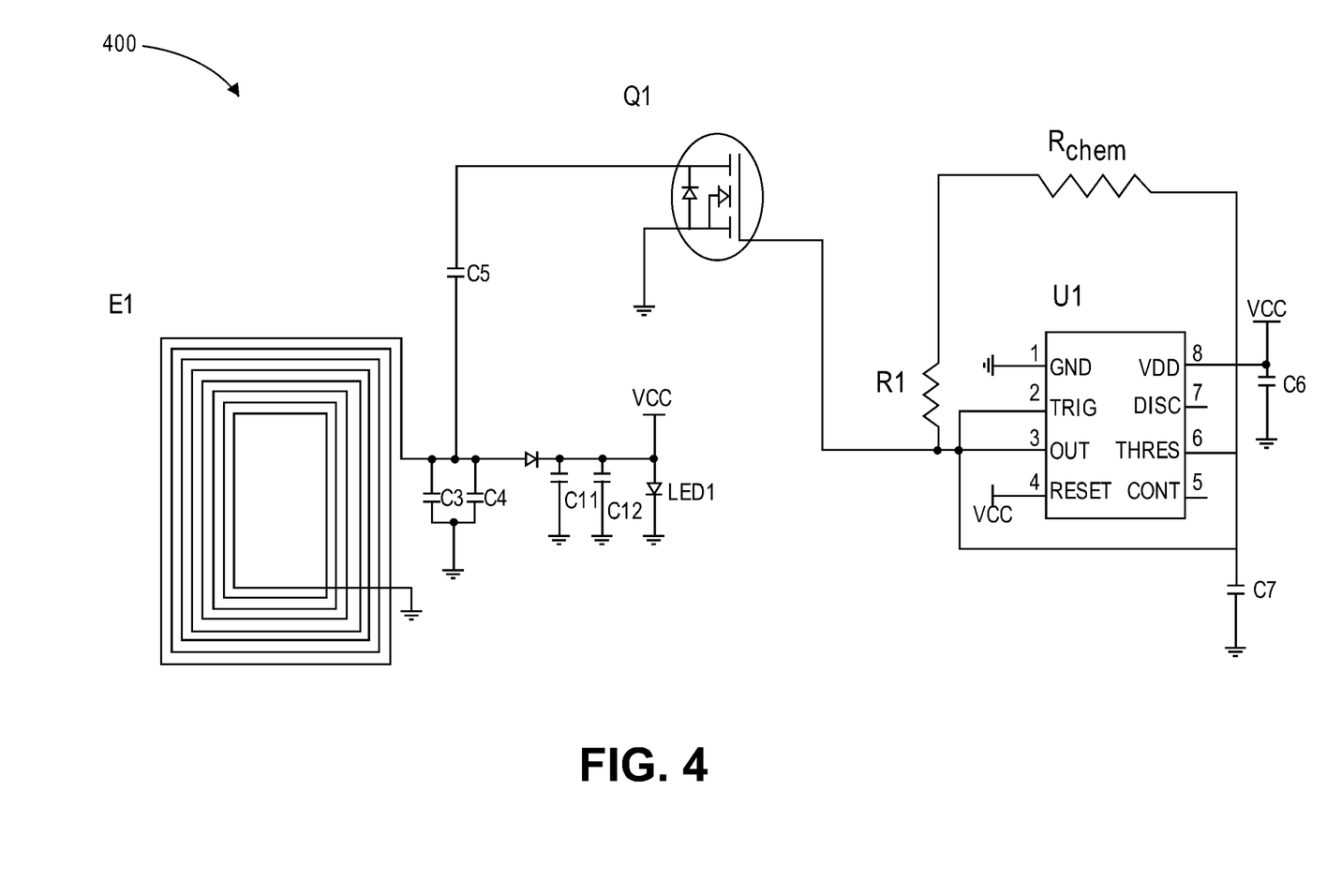
FIG. 4 is a schematic diagram illustrating an exemplary telemetry LC-circuit incorporating a PANI/CB chemiresistor, according to certain embodiments.

Another embodiment of the incontinence sensor 102 comprises a telemetry circuit which includes the versatility of adding an identification (ID) component. Telemetry circuits modulate the interrogating signal from the reader 104 by a frequency proportional to the impedance of the PANI/CB chemiresistor $R_{chem}$. FIG. 4 is a schematic diagram illustrating an exemplary telemetry LC-circuit 400 incorporating the PANI/CB chemiresistor $R_{chem}$. Telemetry circuit 400 comprises an antenna E1, capacitors C3-C6, C11, C12, resistor R1, diode D1, transistor Q1, timer integrated circuit (IC) U1, and the PANI/CB chemiresistor $R_{chem}$.

As illustrated in FIG. 4, a first end of antenna E1 electrically couples to a drain of transistor Q1 via capacitor C5, and electrically couples to an anode of diode D1. A source of transistor Q1 and a second end of antenna E1 each electrically connect to ground. A cathode of diode D1 electrically connects to the power supply voltage VCC. LED1, C11 and C12 each electrically connect between VCC and ground and C11 and C12 each electrically couple between the first end of antenna E1 and ground.

A gate of transistor Q1 electrically connects to the output of timer IC U1, and the series combination of R1 and Rchem electrically connects between the output and the threshold and trigger inputs of timer IC U1. The threshold and trigger inputs of timer IC U1 further couple to ground via capacitor C7. A reset input of timer IC U1 is pulled high by VCC and timer IC is powered between VCC and ground. Capacitor C6 acts as a filter capacitor between VCC and ground for the power input of timer IC U1.

In an embodiment, C11=0.1 µF; C12=1 µF; C3=0.1 µF C4=0.1 µF; C6=0.1 µF; C7=1000 pF; and R1=24 kΩ. In some embodiments, D1 is a Schottky diode, such as, for example, part numbers BAS56, BAS115, or the like. In some embodiments, transistor Q1 is an N-channel depletion mode MOSFET with a body diode, such as, for example, part number FDV301N from Fairchild Semiconductor, or the like. In some embodiments, timer IC U1 is a programmable timer and oscillator, such as, for example part number TLC555CDR from Texas Instruments, and the like.

In some embodiments, LED1 functions as a shunt voltage regulator for the circuit 400. When the sensor or sensor insert is too close to the reader antenna, the rectified voltage rises exponentially and may exceed the tolerance of the timers. LED1 may provide voltage regulation in this situation. For example, LED1 may comprise a red LED which typically has a 1.8 VDC drop. Excess power is converted into photons, not heat, which reduces the burn risk to the person in close proximity to the sensor or sensor insert. In another embodiment, a zener diode functions as a shunt voltage regulator. Also, LED1 can function as a visual indicator to indicate that the circuit 400 is receiving a signal of sufficient strength from the interrogator. Examples of LED1 are part number HSMH-C190 by Avago Technologies and the like.

Telemetry LC-circuit 400 modulates the effective magnetic field generated when the circuit 400 is interrogated by the reader 104. The sensor comprising the telemetry LC-circuit 400 reflects sidebands that are shifted from the frequency of the reader's interrogating signal. The sidebands are generated when a signal with an oscillating frequency from the timer U1 is applied to the gate of the transistor Q1. When the gate voltage reaches approximately 1 V, the impedance across the source-drain drops to approximately 4 ohms, which is significantly less than the antenna impedance. The impedance drop causes a decrease in the magnetic field experienced by the circuit 400. The oscillating frequency of the timer U1 is based at least in part on the resistance or impedance of the PANI/CB chemiresistor $R_{chem}$.

In the above example, the reader 104 transmits a 13.56 MHz signal. In an embodiment, the reader 104 transmits a precise 13.56 MHz signal. In the absence of urine or feces, $R_{chem} \approx 30$ k$\Omega$, and the oscillating frequency from the timer U1 is approximately 25 kHz. The shifted frequencies are approximately 5.87 kHz from the interrogator's 13.56 MHz signal.

In the presence of urine or feces, $R_{chem} \approx 1$ M$\Omega$ and the oscillating frequency from the timer U1 is approximately 600 Hz. The shifted frequencies are approximately 700 Hz from the interrogator's 13.56 MHz signal.

Thus, instead of reflecting the incident RF signal, a new signal which is shifted in frequency based at least in part on the resistance or impedance of $R_{chem}$, is reflected by the telemetry circuit 400. In some embodiments, these reflected shifted signals are recorded and digitized using short band radio technology. The reflected signal can then be correlated to the PANI/CB $R_{chem}$ resistance to determine if an incontinent event occurred.

In some embodiments, the reader 104 determines based on the received signal whether and incontinent event has occurred. In some embodiments, the reader 104 transmits the received signal to a determining device. The determining device determines whether an incontinent event has occurred based on the signal reflected from the telemetry sensor circuit 400. In an embodiment, the determining device comprises a computer processor and memory including computer-executable instructions. In further embodiments, the reader comprises the determining device.

As in the resonant sensor inserts 102 comprising circuit 200, the telemetry sensor inserts 102 comprising circuit 400 are powered by the interrogating RF field. The components of the telemetry circuit 400 are low cost devices. For example, the costs of C1-C7, R1, D1, Q1, LED1, and U1 in the above example are priced at approximately $0.47 per device, making for an economical sensor insert.

Other embodiments of the telemetry circuit 400 may comprise different component values, different components, and different resonant frequencies, which provide different oscillating frequencies from the timer IC and different shifted frequencies without departing from the operation described above.

Some embodiments of the telemetry sensor circuit 400 comprises a second timing element that can serve as an ID signature. The signature can be specific time delay in the sensor insert's response. For example, the second timer IC gates the output clock signal from the first timer IC U1, which is based on the PANI/CB's resistance as described above, to a frequency converter, a delay element, or the like. The reflected signal containing the sensor's data is then delayed by a preset or predetermined time. In some embodiments, the preset time delay can range from milliseconds to seconds. The time delay allows the reader 104 to interrogate multiple sensor inserts simultaneously or approximately simultaneously. Each sensor insert 102 is identified by the time delay of its signal.

For example, the LC-circuit of a first sensor insert 102 will have a time delay of 100 msec and the LC-circuit of a second sensor insert 102 will have a time delay of 200 msec. Since the two circuits operate asynchronously, there will be periods of time when the signals do not overlap. To further reduce data collisions, a short duty cycle transmission can be employed. Thus, delayed timing sequences can be used as a mechanism for assigning an ID component to an LC-circuit of the incontinence sensor device.

In some embodiments, the sensor insert 102 comprises a digital LC-circuit. A ten digit identification number, for example, is assigned to the circuit. The digital LC-circuit can comprise an off-the-shelf digital IC configured to transmit the chemiresistor's impedance and ID number in a digital data stream. Advantages of the digital incontinence sensor are ease of chemiresistor integration, accurate measurement of the PANI/CB chemiresistor impedance, and an ID element.

According to some embodiments, the digital incontinence sensor comprises digital RFID tag or IC, such as, for example, part number MLX90129 from Melexis, and the like. The digital RFID IC is configured to monitor a resistive sensing element electrically coupled to the IC. The digital RFID IC comprises an A/D converter which is configured to digitize the response of a resistive sensor, such as the PANI/CB chemiresistor $R_{chem}$. Upon interrogation by the reader, the digital circuit performs a resistive measurement on the sensor and transmits the measurement in a data stream. The digital circuit contains a numerical ID element and in addition to transmitting the measurement, the digital circuit also transmits the ID in the data stream. In an embodiment with the ID element, the reader or interrogator 104 can read multiple digital incontinence sensor inserts simultaneously or approximately simultaneous.

Advantageously, the Melexis MLX90129 RFID tag employs a cyclic redundancy check to ensure accuracy in the data stream. A disadvantage of the digital RFID ICs is their high power requirements which limit their range and their cost, which is many times that of the resonant LC circuit 200 and the telemetry LC circuit 400.

In other embodiments, the sensor element is not limited to the PANI/CB chemiresistor, but can be any sensor or sensor element, such as, for example, a moisture sensor, metal oxide moisture sensors, capacitance moisture sensors, electrolyte activation moisture sensors, and the like.

In some embodiments, the incontinence sensor insert 102 is placed in the posterior region of the patient's brief to selectively detect feces as fecal incontinence creates a greater risk for IAD, pressure ulcers, and urinary tract infections. In addition, the magnitude of the impedance change in $R_{chem}$ can be used to differentiate between urine and feces. Alternatively, the placement of the sensor insert 102 is in the anterior region of the patient's brief to selectively detect urine.

In some embodiments, the incontinence sensors 102 comprise a flexible substrate patterned with the passive circuit designs disclosed herein. The PANI/CB chemiresistors can be added to the flexible substrate via ink-jet printing of the polymer composite suspension.

In some embodiments, the sensors or sensor inserts 102 are approximately the size of a large postage stamp and are battery free. In other embodiments, the sensors or sensor inserts 102 comprises a battery which extends its readable range. Embodiments of the sensor inserts 102 provide a reliable means for detecting an incontinent event, thereby providing caregiver the awareness for preventing IAD. Further, the sensor inserts provide a convenient and low-cost option for managing incontinence.

Bodily waste sensors may include sensor that are capable of sensing urine, feces, bodily fluid, bodily secretions, signs of infection, such as tissue rot, and yeast, for example, and the like.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

While certain embodiments of the inventions have been described, these embodiments have been presented by way of example only, and are not intended to limit the scope of the inventions. Indeed, the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

What is claimed is:

1. A bodily waste sensor comprising:
   a circuit comprising a polyaniline/carbon black (PANI/CB) composite chemiresistor, an antenna, and a first timer that is energized by an interrogating radio frequency (RF) signal to produce an oscillating signal having a frequency that is based at least in part on an impedance of the PANI/CB composite chemiresistor, the impedance of the PANI/CB composite chemiresistor changes upon exposure to bodily waste.

2. The bodily waste sensor of claim 1 wherein the bodily waste comprises urine and/or feces.

3. The bodily waste sensor of claim 1 wherein the impedance of the PANI/CB composite chemiresistor increases by a factor of approximately $10^5$ when in contact with the bodily waste.

4. The bodily waste sensor of claim 1 wherein the circuit is energized by the interrogating RF signal at a distance of up to 5 meters.

5. The bodily waste sensor of claim 1 being disposable.

6. The bodily waste sensor of claim 1 wherein the circuit comprises a resonant circuit or a flexible circuit.

7. The bodily waste sensor of claim 6 wherein the circuit comprises a resonant circuit and the resonant circuit further comprises an LC-circuit.

8. The bodily waste sensor of claim 7 wherein the oscillating signal is indicative of a quality (Q) factor of the LC-circuit.

9. The bodily waste sensor of claim 8 wherein the Q-factor of the LC-circuit in the presence of the bodily waste is greater than the Q-factor of the LC-circuit in the absence of the bodily waste.

10. The bodily waste sensor of claim 8 wherein the Q-factor of the LC-circuit in the presence of the bodily waste is less than the Q-factor of the LC-circuit in the absence of the bodily waste.

11. The bodily waste sensor of claim 8 wherein the Q-factor of the LC-circuit in the presence of the bodily waste is greater than the Q-factor of the LC-circuit in the absence of the bodily waste by a factor of approximately 2.

12. The bodily waste sensor of claim 8 wherein the Q-factor of the LC-circuit is proportional to the impedance of the PANI/CB composite chemiresistor.

13. The bodily waste sensor of claim 7 wherein the LC-circuit comprises at least one capacitor, at least one inductor and at least one resistor configured in parallel, the at least one resistor comprising the PANI/CB composite chemiresistor.

14. The bodily waste sensor of claim 13 wherein the at least one resistor comprises the PANI/CB composite chemiresistor in series with a second resistor.

15. The bodily waste sensor of claim 1 wherein the circuit comprises a telemetry circuit.

16. The bodily waste sensor of claim 15 wherein the telemetry circuit further comprises at least one transistor.

17. The bodily waste sensor of claim 16 wherein the oscillating signal from the first timer is applied to a gate of the at least one transistor to modulate a magnetic field induced by the interrogating RF signal.

18. The bodily waste sensor of claim 15 wherein a response signal from the telemetry circuit comprises sideband signals shifted in frequency from a frequency of the interrogating RF signal, a frequency of the sideband signals based at least in part on the impedance of the PANI/CB composite chemiresistor.

19. The bodily waste sensor of claim 18 wherein the telemetry circuit comprises a second timer configured to delay the response signal from the telemetry circuit by a predetermined amount of time, the predetermined amount of time comprising a unique identifier.

20. The bodily waste sensor of claim 1 wherein a response signal from the circuit comprises sideband signals shifted in frequency from a frequency of the interrogating RF signal, a frequency of the sideband signals based at least in part on the frequency of the oscillating signal from the first timer.

21. The bodily waste sensor of claim 1 wherein the bodily waste sensor is configured to receive the interrogating RF signal, and send a response signal in response to the interrogating RF signal, the response signal based at least in part on the impedance of the PANI/CB composite chemiresistor.

22. The bodily waste sensor of claim 21 wherein the response signal is indicative of a quality (Q) factor, a higher Q-factor indicating an incontinent event and a lower Q-factor indicating absence of the incontinent event.

23. The bodily waste sensor of claim 21 wherein the response signal is shifted in frequency from a frequency of the interrogating RF signal, the frequency shift dependent upon at least the impedance of the PANI/CB composite chemiresistor.

24. The bodily waste sensor of claim 21 wherein the interrogating RF signal powers the bodily waste sensor.

25. The bodily waste sensor of claim 21 wherein the response signal is analyzed to determine whether urine and/or feces are present.

26. A bodily waste sensor comprising:
   a resonant LC-circuit comprising a polyaniline/carbon black (PANI/CB) chemiresistor, an antenna, and a timer that is energized by an interrogating radio frequency (RF) signal to produce an oscillating response signal, a frequency of the oscillating response signal based at least in part on an impedance of the PANI/CB chemiresistor that changes upon exposure to bodily waste.

\* \* \* \* \*